United States Patent [19]

Den Braber et al.

[11] Patent Number: 4,925,657

[45] Date of Patent: May 15, 1990

[54] INSECTICIDAL COMPOSITION AND METHOD FOR COMBATTING APHIDS

[75] Inventors: Antonie A. Den Braber, Putten; Evert R. Slootweg, Stroe, both of Netherlands

[73] Assignee: Denka International B.V., Voorthuizen, Netherlands

[21] Appl. No.: 70,137

[22] Filed: Jun. 29, 1987

Related U.S. Application Data

[63] Continuation of Ser. No. 815,619.

[30] Foreign Application Priority Data

Jan. 4, 1985 [NL] Netherlands .......................... 8500015

[51] Int. Cl.$^5$ ...................... A61L 9/04; A01N 25/00; A01N 57/00; A01N 57/26
[52] U.S. Cl. .................................... 424/45; 424/84; 514/65; 514/86; 514/122; 514/132; 514/136; 514/147; 514/275; 514/431; 514/477; 514/479; 514/490; 514/521; 514/531; 514/762; 514/919
[58] Field of Search .................. 424/84, 45; 514/762, 514/919, 65, 86

[56] References Cited

U.S. PATENT DOCUMENTS

| | | | |
|---|---|---|---|
| 2,761,805 | 9/1956 | Huidobro et al. | 514/755 |
| 4,178,384 | 12/1979 | Ensing | 514/919 |
| 4,505,934 | 3/1985 | Gut et al. | 514/762 |
| 4,546,110 | 10/1985 | Dawson et al. | 514/529 |

FOREIGN PATENT DOCUMENTS 0121363 10/1984 European Pat. Off. .
8103905 of 1981 Netherlands .

OTHER PUBLICATIONS

Chemical Abstracts 101:105760e, (1984).
Chemical Abstracts 93:90177k (1980).
Griffiths et al., Ent. Exp. & Appl. 27, (1980), 199–201.
Griffith et al., "Behavior of Alatae of *Myzus persicae* (Hemiptera:Aphididae) on Chemically Treated Surfaces after Tethered Flight", *Bio. Abstr.*, vol. 76, No. 5, 1983, 31073.
Griffith et al., "A Potential Application of Aphid Alarm Pheromones", *Ent. Exper. et Appl.*, vol. 27, No. 2, 1980, pp. 199–201.

*Primary Examiner*—Allan J. Robinson
*Attorney, Agent, or Firm*—Browdy & Neimark

[57] ABSTRACT

The invention provides insecticidal compositions for combatting aphids, which compositions contain an aphid insecticide in an amount lower than the minimum usual percentage for said insecticide in an aphicidal composition and an alarm pheromone for aphids. The compositions of the invention are less toxic because of the reduced insecticide content but they are not less effective than the insecticidal compositions which do not contain an alarm pheromone.

17 Claims, No Drawings

INSECTICIDAL COMPOSITION AND METHOD FOR COMBATTING APHIDS

This application is a continuation, of application Ser. No. 815,619, filed Jan. 2, 1986, abandoned.

This invention relates to insecticidal compositions and to a method for combatting aphid.

It is known that the use of insecticides suffers from disadvantages because of the toxicity of insecticides.

From PCT application WO-A-8204249 it is known to use both E-β-farnesene, an aphid alarm pheromone, and an insecticide (aphicide). Practical examples of this combination are not disclosed in said PCT-application. In Entomoligia Experimentalis et Applicata, vol. 27, no. 2, 1980, blz. 199–201, "Ned. Entomol. Ver., Amsterdam", A potential application of aphid alarm pheromones" by D. C. Griffiths en J. A. Pickett, which does disclose a practical embodiment of this combination, the two materials are used successively and not in one composition.

The insecticidal composition according to the invention contains 0.05–4.0 percent by weight of an alarm pheromone for aphids and an aphid insecticide in an amount which is at least about 10% less than the minimum usual amount for said insecticide in an aphicidal composition.

An advantage of the present invention is that by using an alarm pheromone for aphids in combination with an insecticide, the amount of insecticide can be considerably less, i.e. at least about 10% less than the minimum usual amount of said insecticide in an aphicidal composition.

The activity of the alarm pheromone is due to the fact that the aphids begin to move as a result of the agitation caused by the alarm pheromone, whereby the contact with the insecticide is promoted and furthermore the aphids fall from the plants in great numbers and the majority will not find again the plant; in addition, the agitation brought about by the alarm pheromone causes as such inactivation ("knock down") of the insects, after which the insects often die.

In general when using the present mixture of aphid insecticide and alarm pheromone a faster killing can be observed than when using only the insecticide.

Furthermore, the present mixture is active against aphid strains which are resistant to organic phosphates, carbamates and pyrethroids, even though the amount of insecticide in the mixture is less than the usual amount.

In addition, the replacement of part of the insecticide by an alarm pheromone generally means a cost saving such as in the case of the combination pyrethrum/farnesene.

As alarm pheromones for aphids E-β-farnesene and α-pinene may be mentioned.

Preferably the amount of the aphid insecticide in said composition is about 20% less than the minimum amount which is usual for said insecticide.

When using pyrethrum (a mixture of natural pyrethroids) as the aphid insecticide, this insecticide is used in an amount which is at least about 10% less than 0.06 percent by weight, the minimum usual percentage of pyrethrum in aphidical compositions.

When using a synthetic pyrethroid as the aphid insecticide (e.g. tetrametrin, alletrin, permetrin, cypermetrin, deltametrin) as the aphid insecticide, this insecticide is used in an amount which is at least about 10% less than 0.03% by weight, the minimum usual percentage of a synthetic pyrethroid in aphicidal compositions.

When using organic chloro compounds, organic phosphates or carbamates (e.g. endosulfan, fenitrothion, butocarboxim, bromofos, DDVP, diazinon, malathion, pirimicarb, propoxur and ethiofencarb) as the aphid insecticides, these insecticides are used in an amount which is at least about 10% less than 0.05% by weight, the minimum usual percentage of these insecticides in aphicidal compositions.

According to the invention the insecticide content in the aphicidal composition generally can be lowered by about 75% or more without a disadvantageous influence on the activity. For example the minimum usual percentage of synthetic pyrethroids in aphicidal compositions is about 0.03% and in the present mixtures this percentage can be lowered to about 0.01% without detracting from the activity. For the combination pyrethrum/farnesene the lower limit for the amount of pyrethrum in an aerosol formulation is only 0.00025% and the practical upper limit is 0.03% (more than 0.03% offers no advantages).

EXAMPLES

Hereinafter a number of spray tests with aphids are carried out.

Spraying was carried out with aerosol cans containing water-based compositions, of which the data concerning the amounts of pyrethrum and E-β-farnesene are mentioned in table 1. (It is also possible to prepare other compositions than water-based compositions, e.g. methanol-based compositions). Furthermore the compositions contain a butane/propane mixture as the propellent gas, piperonyl butoxide (an insecticidal synergistic agent), the pyrethrum:piperonyl butoxide ratio being 1:5, and an emulsifier (nonylphenol having an average of 8–9 ethylene oxide units).

TABLE 1

Pyrethrum- and farnesene concentrations in aerosol cans.

| Composition | Concentrations, %* | | | | | |
|---|---|---|---|---|---|---|
| pyrethrum (25%) | | | 0.12 | 0.06 | 0.03 | 0.015 |
| pyrethrum (25%)/ farnesene | 0.48/0.10 | 0.24/0.10 | 0.12/0.10 | 0.06/0.10 | 0.03/0.10 | 0.015/0.10 |
| farnesene | 0.10 | | | | | |

*The real concentrations of pyrethrum are in all cases lower by a factor of 4 because in all cases 25% pyrethrum standard solutions were initially used.

The following aphids were used for the tests:
the pea aphid, *Acyrthosiphon pisum*
the green peach aphid, *Myzus persicae* (strains $M_1$, $M_2$ and "IPO-resistant", $M_2$ is a highly organic phosphate-resistant strain and "IPO-resistant" is a strain which is generally resistant to organic phosphates, carbamates and pyrethroids; ("IPO" means "Instituut voor Plantenziektenkundig Onderzoek")
the bean aphid, *Aphis fabae*
the potato aphid, *Macrosiphon euphorbiae*
a species living on ferns, *Idiopterus nephrolepidis*

The mortality was determined 2 hours and 24 hours after treatment of the aphids. When permanently motionless the aphid was considered dead. This was concluded from the reaction of the aphids when touched with a brush, observed with a microscope. During the tests two petri-dishes with 20 aphids on filter paper, which were not sprayed, were placed in the experimental room in order to investigate the influence of external factors on the mortality.

Example 1

Tests with aphids on filter paper.

10 Petri-dishes per test were used; 5 for spraying with pyrethrum and 5 for spraying with the combination pyrethrum/farnesene. The petri-dishes had a diameter of 110 mm; the edge was coated with fluon (a dispersion of polytetra fluoro ethylene, ICI) in order to prevent the aphids from running away. On the bottom of each dish a filter paper having a diameter of 110 mm (Schut type V 255) was present. Into each petri-dish 20 aphids were brought (from larvae of the third stage to matured).

In one series of tests the aphids were directly sprayed. This was carried out vertically at a distance of about 30 cm. The spray times were in all cases the same (about 6 seconds). After 2 and 24 hours the percentage of mortality was determined by counting the number of dead and living aphids.

Also tests employing in direct spraying were carried out, the filter paper being sprayed first and thereafter the aphids were brought into the petri-dishes.

The results of these tests are summarized in tables 2 and 3.

TABLE 2

Results of direct spraying of aphids on filter paper (vide also footnote table 1)

| Species | Compositions | % Mortality after 2 hours | % Mortality after 24 hours |
|---|---|---|---|
| A. *Ac. Pisum* | 0.015% pyr. | 30% | 100% |
|  | 0.015% pyr./0.1% farn. | 100% | 100% |
| B. *Ac. Pisum* | Dist. H$_2$O | 0% | 0% |
|  | 0.00% pyr./0.1% farn. | 30% | 72% |
| *C. *Ac. Pisum* | blank | 10% | 27.5% |
|  | 0.00% pyr./0.1% farn. | 25% | 53% |
| D. *Myzus persicae* | 0.03% pyr. | 30% | 100% |

TABLE 2-continued

Results of direct spraying of aphids on filter paper (vide also footnote table 1)

| Species | Compositions | % Mortality after 2 hours | % Mortality after 24 hours |
|---|---|---|---|
| (IPO-resistant) | 0.03% pyr./0.1% farn. | 70% | 100% |

According to the CHI-square test the differences found in tests A, B, C and D are significant.

*In test C "blank" means water + emulsifier.

TABLE 3

Results of indirect spraying of aphids on filter paper (vide also footnote 25 table 1)

| Species | Composition | % Mortality after 2 hours | % Mortality after 24 hours |
|---|---|---|---|
| *Ac. Pisum* | 0.015% pyr. | 20% | 100% |
|  | 0.015% pyr./0.1% farn. | 40% | 100% |

From the above results the following appears:
(1) The combination aphid insecticide/pheromone has even a better activity than the insecticide alone (faster killing).
(2) The use of only the pheromone also results in a certain percentage of dead aphids.

Example 2

Tests with aphids on leaves and plants

A leave (vide table 4 for the plant species) having a known number of aphids (all stages of development) was put into the petri-dish. The aphids were sprayed as described for the direct spraying of aphids on filter paper. After the treatment the number of living and dead aphids were again determined after 2 and 24 hours and converted to percentages.

Furthermore different plant species (vide table 5) having aphids were sprayed from 4 sides at a distance of about 30 cm. Plants having a leave surface of 300–500 cm$^2$ and an estimated aphid population of 150 aphids per 100 cm$^2$ were selected. Under the plant black card board was placed in order to observe the falling aphids. Thereafter leaves were cut from the plants and stored in petri-dishes having a fluon edge, in order to determine the mortality. Also tests were carried out wherein the aphid mortality on the whole plant was determined.

TABLE 4

Results of spraying aphids on leaves (vide also footnote table 1)

| Aphid species | Plant species | Composition | Mortality 2 hours | Mortality 24 hours | Remark |
|---|---|---|---|---|---|
| A. *Myzus persicae* M$_1$ | Chinese cabbage | 0.12% pyr. | 50% | 100% | 200 aphids per leave of 50 cm$^2$ |
| *Myzus persicae* M$_1$ | Chinese cabbage | 0.12% pyr./0.1% farn. | 80% | 100% | 200 aphids per leave of 50 cm$^2$ |
| B. *Myzus persicae* M$_2$ | Cole seed | blank | n.d. | 28% | 210 aphids per leave of 70 cm$^2$ |
| *Myzus persicae* M$_2$ | Cole seed | 0.00% pyr./0.1% farn. | n.d. | 82% | 170 aphids per leave of 70 cm$^2$ |
| C. *Myzus persicae* M$_1$ + M$_2$ | Cole seed | 0.06% pyr. | 40 | 100% | 120 aphids per leave of 60 cm$^2$ |
| *Myzus persicae* M$_1$ + M$_2$ | Cole seed | 0.06% pyr./0.1% farn. | 60% | 100% | 160 aphids per leave of 60 cm$^2$ |
| D. *Ac. Pisum* | Broad beans | 0.06% pyr. | 85[2] | 100% | 5 × 20 aphids per leave |
| *Ac. Pisum* | Broad beans | 0.06% pyr./0.1% farn. | 100[2] | 100% | 5 × 20 aphids per leave |
| E. *Macr. Euphorbiae* | Hibiscus sp. | 0.015% pyr./0.1% farn. | n.d. | 100% | On the topleaves and the blossoms a large population of aphids, about 20–30 per leave |
| F. *Macr. Euphorbiae* | Hibiscus sp. | blank | 0% | 0%[1] | On the topleaves and the blossoms a large population af aphids, about 20–30 per leave |

[1] no visible mortality observed.
[2] determined after 1 hour
n.d. = not determined.

TABLE 5

Results of spraying aphids on plants (vide also footnote 1)

| Aphid Species | Plant species | Composition | Mortality 2 hours | Mortality 24 hours | Remark |
|---|---|---|---|---|---|
| A. *Myzus persicae* (IPO-resistant) | Cole seed | 0.015% pyr. | 30% | 90% | aphids fall from the plant |
| | | 0.015% pyr./0.1% farn. | 70% | 100% | |
| B. *Idiopterus Nephrolepidis* | Fern | 0.12% pyr. | 50% | 100% | no falling aphids observed |
| | | 0.12% pyr./0.1% farn. | 75% | 100% | great number of aphids fall from the plant |
| C. *Aphis fabae* | Broad bean | 0.12% pyr. | 70% | 100% | aphids fall sporadically |
| | | 0.12% pyr./0.1% farn. | 80% | 100% | aphids fall sporadically but run away |
| D. *Myzus persicae* (IPO-resistant) | Radish | 0.015% pyr. | 40% | 90% | 5 plants having 5 leaves per test and about 500 aphids per leave aphids fall from the plant |
| | | 0.015% pyr./0.1% farn. | 70% | 100% | | n.d. not determined.

TABLE 6

Results from spraying aphids on plants (vide footnote table 1). Per test: 5 plants (broad beans) having 20 aphids (*A. pisum*) per plant. Spraying time about 6 seconds.

| Composition | Mortality after 19 hours |
|---|---|
| 0.004% pyrethum (25%) | 17 dead aphids |
| | 12 dead aphids |
| | 13 dead aphids |
| | 14 dead aphids |
| | 15 dead aphids |
| | Average 71%, varies between 60 and 85% |
| 0.004% pyrethum (25%), 0.1% E-β-farnesene | 17 dead aphids |
| | 17 dead aphids |
| | 20 dead aphids |
| | 18 dead aphids |
| | 19 dead aphids |
| | Average 91%, varies between 90 and 100% |

When spraying plants, no damage to the plants was observed for any of the compositions; there was some damage to the fern (table 5), but in this case recovery occured later.

Also from tables 4, 5 and 6 it appears that the combination aphid insecticide/pheromone gives a faster killing than only the insecticide and that the use of only the pheromone also results in a certain percentage of dead aphids. Furthermore the combination aphid insecticide/farnesene appears to have a superior activity for resistant aphids (table 4).

From table 5 it appears that by using farnesene the aphids fall from the plant.

We claim:

1. An aphicidal composition containing a synergistically effective amount of 0.05–4.0% by weight of E-beta-farnesene, and an aphicidal insecticide in an amount ranging from the minimum amount of said aphicidal insecticide effective to kill aphids when said recited amount of said alarm pheromone is present to about 10% less than the minimum amount of said aphicidal insecticide effective to kill aphids when said aphicidal insecticide is used as a sole active ingredient in an aphicidal composition, wherein said aphicidal insecticide is selected from the group consisting of organic chloro insecticides, organic phosphate insecticides, carbamate insecticides, and pyrethroid insecticides.

2. The composition of claim 1, wherein said insecticide is selected from the group consisting of endosulfan, fenitrothion, butocarboxim, bromofos, DDVP, diazinon, malathion, pirimicarb, propoxur and ehtiofencarb in an amount which is at least about 10% less than 0.05% by weight.

3. The composition of claim 1, wherein said aphicidal insecticide is an organic chloro compound in an amount which is at least about 10% less than 0.05% by weight.

4. The composition of claim 1, wherein said aphicidal insecticide is an organic phosphate compound in an amount which is at least about 10% less than 0.05% by weight.

5. The composition of claim 1, wherein said aphicidal insecticide is a carbamate compound in an amount which is at least about 10% less than 0.05% by weight.

6. A composition according to claim 1, containing a synthetic pyrethroid as said aphicidal insecticide in an amount which is at least about 10% less than 0.03% by weight.

7. A composition according to claim 1 in the form of an aerosol.

8. A composition according to claim 1, containing said aphicidal insecticide in an amount which is at least about 20% less than said minimum effective amount for said aphicidal insecticide as the sole active ingredient.

9. A composition according to claim 1, containing pyrethrum as said aphicidal insecticide in an amount which is at least about 10% less than 0.06% by weight.

10. A method for combatting aphids comprising the step of spraying on leaves an aphicidal composition containing a synergistically effective amount of 0.05–4.0% by weight of E-beta-farnesene, and an aphicidal insecticide in an amount ranging from the minimum amount of said aphicidal insecticide effective to kill aphids when said recited amount of said alarm pheromone is present to about 10% less than the minimum amount of said aphicidal insecticide effective to kill aphids when said aphicidal insecticide is used as a sole active ingredient in an aphicidal composition, wherein said aphicidal insecticide is selected from the group consisting of organic chloro insecticides, organic phosphate insecticides, carbamate insecticides, and pyrethroid insecticides.

11. The method of claim 10, wherein said composition contains said aphicidal insecticide in an amount which is at least about 20% less than said minimum effective amount when said aphicidal insecticide is the sole active ingredient.

12. The method of claim 10, wherein said composition contains pyrethrum as said aphicidal insecticide in an amount which is at least about 10% less than 0.06% by weight.

13. The method of claim 10, wherein said composition contains a synthetic pyrethroid as said aphicidal insecticide in an amount which is at least about 10% less than 0.03% by weight.

14. The method of claim 10, wherein said aphicidal insecticide is an organic chloro compound in an amount which is at least about 10% less than 0.05% by weight.

15. The method of claim 10, wherein said aphicidal insecticide is an organic phosphate compound in an amount which is at least about 10% less than 0.05% by weight.

16. The method of claim 10, wherein said aphicidal insecticide is a carbamate compound in an amount which is at least about 10% less than 0.05% by weight.

17. The method of claim 10, wherein said composition contains as said aphicidal insecticide a member selected from the group consisting of endosulfan, fenitrothion, butocarboxim, bromofos, DDVP, diazinon, malathion, pirimicarb, propoxur and ethiofencarb in an amount which is at least about 10% less than 0.05% by weight.

* * * * *